United States Patent
Seifert et al.

[11] Patent Number: 5,900,215
[45] Date of Patent: * May 4, 1999

[54] FIBER OPTIC SENSOR

[75] Inventors: Kevin R. Seifert, Forest Lake; Laurie Lynch, Eden Prairie; Debra K. Johnson, Andover; Jonathan Kalla, St. Louis Park; William Fowler, Minneapolis, all of Minn.

[73] Assignee: Optical Sensors Incorporated, Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/855,939

[22] Filed: May 14, 1997

Related U.S. Application Data

[62] Division of application No. 08/524,592, Sep. 7, 1995, Pat. No. 5,656,241.

[51] Int. Cl.$^6$ ................................ G01N 21/64
[52] U.S. Cl. ............................ 422/82.07; 356/39
[58] Field of Search ................... 422/82.05, 82.06, 422/82.07, 82.08, 91; 385/12; 427/163.2; 356/39

[56] References Cited

U.S. PATENT DOCUMENTS

| | | |
|---|---|---|
| Re. 31,879 | 5/1985 | Lubbers et al. . |
| 4,577,109 | 3/1986 | Hirschfeld . |
| 4,785,814 | 11/1988 | Kane . |
| 4,842,783 | 6/1989 | Blaylock . |
| 4,889,407 | 12/1989 | Markle et al. . |
| 4,954,318 | 9/1990 | Yafuso et al. . |
| 5,047,208 | 9/1991 | Schweitzer et al. ............ 422/82.06 |
| 5,120,510 | 6/1992 | Gourley et al. ............ 422/82.07 |
| 5,152,287 | 10/1992 | Kane . |
| 5,271,073 | 12/1993 | Hui et al. ............................ 385/12 |
| 5,277,872 | 1/1994 | Bankert et al. . |
| 5,326,531 | 7/1994 | Hahn et al. . |
| 5,354,825 | 10/1994 | Klainer et al. . |
| 5,508,509 | 4/1996 | Yafuso et al. ............ 422/82.05 |
| 5,591,400 | 1/1997 | Dektar et al. ............ 422/57 |

FOREIGN PATENT DOCUMENTS 481740 4/1992 European Pat. Off. .

OTHER PUBLICATIONS

Fuh et al., "Single Fibre Optic Fluorescence pH Probe," *Analyst* (1987) 112:1159–1163.

Goldstein et al., "A Miniature Fiber Optic pH Sensor for Physiological Use," *J. Biomechanical Eng.* (1980) 102:141–146.

Hirschfeld et al. "Laser– Fiber–Optic 'Optrode' for Real Time in vivo Blood Carbon Dioxide Level Monitoring," *Jrnl of Lightwave Technology* (1987) LT5:1027–1033.

Jones et al., "A Field–Deployable Dual–Wavelength Fiber–Optic pH Sensor Instrument Based on Solid–State Optical and Electrical Components," *Applied Spectroscopy* (1991) 45 (8):1271–1277.

Jones et al., "Optical pH Sensor Based on the Chemical Modification of a Porous Polymer Film," *Anal. Chem.* (1988) 60:404–406.

Jordan et al., "Physiological pH Fiber–Optic Chemical Sensor Based on Energy Transfer," *Amer. Chem.* (1987) 59 (3):437–439.

(List continued on next page.)

*Primary Examiner*—Jeffrey Snay
*Attorney, Agent, or Firm*—Dianne E. Reed; Bozicevic & Reed LLP

[57] ABSTRACT

A method is provided for manufacturing a fiber optic sensor for detecting or measuring a parameter of interest in a sample fluid, including pH, concentration of dissolved gases such as $O_2$ or $CO_2$, and the like. The sensing chemistry is affixed to the distal end of an elongated optical fiber by way of an adhesive layer typically comprised of an acrylic adhesive composition. Novel optical sensors, fabricated using the aforementioned method, are provided as well.

18 Claims, 3 Drawing Sheets

OTHER PUBLICATIONS

Liu et al., "Development of a Porous Polymer pH Optrode," *Optics Letters* (1992) 17 (24):1815–1817.

Maher et al., "A Fiber Optic Chemical Sensor for Measurement of Groundwatr pH," *Journal of Testing and Evaluation* (1993) 448–452.

Moreno et al., "Analytical Performance of an Optical pH Sensor for Acid–Base Titration," *Analytica Chimica Acta* (1990) 230:35–40.

Motellier et al., "Fiber–Optic pH Sensor for in situ Applications," *Sensors and Actuators B* (1993) 11:467–473.

Munkholm et al., "Polymer Modification of Fiber Optic ChemicalSensors as a Method of Enhancing Fluorescence Signal for pH Measurement," *Anal. Chem.* (1986) 58:1427–1430.

Peterson et al., "Fiber Optic pH Probe for Physiological Use," *Anal. Chem.* (1980) 52 (6):864–869.

Posch et al., "Towards a Gastric pH–Sensor: an optrode for the pH 0–7 Range," *Fresnius Z. Anal. Chem.* (1989) 334:162–165.

Seitz, "Chemical Sensors Based on Fiber Optics," *Analytical Chemistry* (1984) 56(1):16A–34A.

Serra et al., "Fibre–Optic pH Sensor for Sea–Water Monitoring Using a Single Dye," *Analytica Chimica Acta* (1990) 232:337–344.

Wolfbeis et al., "Recent Progress in Optical Oxygen Sensing," *SPIE Optical Fibers in Medicine III* (1988) 906:42–48.

Wolfbeis et al., "LED–Compatible Fluorosensor for Measurement of Near–Neutral pH Values," *Mikrochim. Acta* (1992) 108:133–141.

FIBER OPTIC SENSOR

CROSS-REFERENCE TO RELATED APPLICATIONS

This is a divisional of U.S. patent application Ser. No. 08/524,592, filed Sep. 7, 1995, issued Aug. 12, 1997 as U.S. Pat. No. 5,656,241.

TECHNICAL FIELD

The present invention relates generally to fiber optic sensors for measuring one or more parameters of a sample fluid. More particularly, the invention relates to a novel method for manufacturing such optical sensors and to the sensors formed thereby. The sensors are useful, inter alia, for the measurement of pH and detection and quantitation of gases such as oxygen and carbon dioxide.

BACKGROUND

Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location. Structures, properties, functions and operational details of fiber optic chemical sensors can be found in U.S. Pat. No. 4,577,109 to Hirschfeld, U.S. Pat. No. 4,785,814 to Kane, and U.S. Pat. No. 4,842,783 to Blaylock, as well as Seitz, "Chemical Sensors Based on Fiber Optics," *Analytical Chemistry* 56(1):16A–34A (1984), each of which is incorporated by reference herein.

Publications such as these generally illustrate that it is known to integrate a chemical sensor with a fiber optic waveguide, an electrochemical gas sensor or the like, in a manner such that the chemical sensor will interact with the analyte. This interaction results in a change in optical properties, which change is probed and detected through the fiber optic waveguide or the like. These optical properties of chemical sensor compositions typically involve changes in colors or in color intensities. In these types of systems, it is possible to detect particularly minute changes in the parameter or parameters being monitored in order to thereby provide especially sensitive remote monitoring capabilities. Chemical sensor compositions that are incorporated at the distal end of fiber optic sensors are often configured as membranes that are secured at the distal tip end of the waveguide device or optrode.

Gas sensors of this general type are useful in monitoring gas concentrations such as oxygen and carbon dioxide in bloodstreams and the like. Also, it is sometimes desirable to provide sensors that monitor other parameters such as pH. Ion concentrations can also be detected, such as potassium, sodium, calcium and metal ions.

A typical fiber optic sensor device positions the sensor material at a generally distal location with the assistance of one or more types of support means. Support means must be such as to permit interaction between a parameter-sensitive indicator—e.g., a fluorescent dye or the like—and the substance being subjected to monitoring, measurement and/or detection. Known approaches in this regard include the use of permeable membranes and composites incorporating micro-encapsulation.

One example of such an approach is found in U.S. Pat. No. RE 31,879 to Lubbers et al. That patent discloses a device wherein indicator material is provided in solution form and separated from the external environment by a membrane. This approach has been followed more recently by a number of others working in the field as well.

An alternative approach has been to attach an indicator composition to the tip of an optical fiber using a silanization technique. This method generally involves silanization of beads of porous glass, followed by covalent bonding of the indicator material to functional groups extending from the glass beads (generally through a siloxane linkage, as shown, for example, in U.S. Pat. No. 5,354,825 to Klainer et al.), in turn followed by attachment of the glass beads to the optical fiber. This technique, however, suffers from several drawbacks. For example, attachment of the glass beads to the fiber can be difficult because of the small size of the beads and the ease with which the pores in the glass are occluded. Additionally, these types of sensors cannot be extensively exposed to aqueous solutions, as glass dissolution and indicator leaching will occur through hydrolysis of siloxane linkages.

Still another technique involves direct bonding of photoactive polymers to the tip of an optical fiber, as described in U.S. Pat. No. 5,354,825 to Klainer et al., referenced above. While this method is effective, there nevertheless remains a need in the art for alternative methods of providing indicator materials on a fiber optic sensor device which are reliable, highly sensitive, simple to carry out and readily scaled up for purposes of manufacture.

The present invention provides such a method, and involves the use of an adhesive layer for affixing an indicator composition (sometimes referred to herein as "sensing chemistry") to the distal end of a fiber optic sensor. The method involves simple coating and curing procedures, and is thus straightforward to carry out. Additionally, the novel method enables control of sensor tip geometry, provides a protective layer for the fiber tip, and enables spatial partitioning of materials incorporated into the sensing area, e.g., indicator and reference dyes or the like. As will be explained in detail herein, the method also enables the use of more indicator at the sensor tip by increasing the available surface area to which an indicator-containing composition can bind, and provides for better adhesion of the indicator composition to the sensor surface, through either chemical bonding, mechanical adhesion, or both. A very reliable and highly sensitive sensor device is thus provided in which the likelihood of leaching and/or delamination of the indicator composition is minimized.

OTHER PERTINENT ART

In addition to the references mentioned in the preceding section, the following relate to methods for providing indicator materials in fiber optic sensors:

Schirone et al., *Analytica Chimica Acta* 232:337–344 (1990), Motellier et al., *Sensors and Actuators* B 11:467–473 (1993), Moreno et al., *Analytica Chimica Acta* 230:35–40 (1990), Wolfbeis et al., *Fresnius Z. Anal. Chem.* 334:162–165 (1989), Wolfbeis et al., *SPIE Optical Fibers in Medicine III* 906:42–48 (1988) and Hirschfeld et al., *Analyst* 112:1159–1163 (1987), all relate to sensors in which dye-filled porous beads or ion exchange resins are attached to an optical fiber. In general, the present invention has been found to be advantageous relative to these sensors, which have been found to be sensitive to ion effects and glass dissolution.

Walt et al., *Anal. Chem.* 58:1427–1430 (1986), Walt et al., *Anal. Chem.* 59:437–439 (1987), U.S. Pat. No. 5,277,872 to Hui et al. and European Patent Publication 481,740 describe the use of silane primers in bonding indicator materials to optical fibers. In contrast to these sensors, the present invention avoids the use of hydrolytically unstable materials which are generally difficult to deposit evenly on any given surface.

Peterson et al., *Anal. Chem.* 52:864–869 (1980), Peterson et al., *J. Biomechanical Eng.* 102:141–146 (1980), Maher et al., *Journal of Testing and Evaluation* 443–452 (19983), Liu et al., *Optics Letters* 17:1815–1817 (1992), Jones et al., *Applied Spectroscopy* 45:1271 (1991), Jones et al., *Anal. Chem.* 60:404–406 (1988) and Wolfbeis et al., *Mikrochim. Acta* 108:133–141 (1992), describe methods for attaching sensor chemistry to a fiber optic device in which hollow fibers and/or dialysis membranes are used.

U.S. Pat. No. 5,120,510 to Gourley describes a fiber optic sensor which contains a fluorescent dye within a polymeric matrix located at the tip of the device. An adhesive layer is included to bond a glass sleeve to the fiber tip to increase stiffness or strength of the distal end of the device.

SUMMARY OF THE INVENTION

Accordingly, it is a primary object of the invention to address the above-mentioned needs in the art by providing a novel method for making a fiber optic sensor which has improved sensitivity and reliability.

It is another object of the invention to address these needs by providing a method for making an optical sensor which involves binding a layer of a curable adhesive composition to the tip of an optical fiber, partially or fully curing the adhesive layer so provided, and coating the adhesive layer with an outer layer of an indicator-containing composition, i.e., a composition containing the "sensing chemistry."

It is still another object of the invention to provide such a method which involves incorporation of a reference dye into the adhesive layer, the sensing layer, or both.

It is yet another object of the invention to provide novel optical sensors prepared using the techniques disclosed and claimed herein.

It is a further object of the invention to provide such sensors which are useful in the measurement of various parameters in physiological fluids, such as determination of pH, $pO_2$ or $PCO_2$ in blood.

Additional objects, advantages and novel features of the invention will be set forth in part in the description which follows, and in part will become apparent to those skilled in the art upon examination of the following, or may be learned by practice of the invention.

In one aspect of the invention, a method for making a fiber optic sensor is provided which involves sequentially providing two or more layers of material at the tip of an optical fiber. The innermost layer is an adhesive layer which adheres to the exposed fiber surface and to a cladding material, if present. The adhesive layer may contain some sort of dye or indicator material, preferably a substantially analyte-insensitive reference dye, and comprises a polymeric material which is partially or fully cured prior to application of additional layers. Overlaying this adhesive layer is a further layer, containing analyte-sensitive materials, also sometimes termed herein the "sensing chemistry." Additional layers may in some cases be present; whether or not such layers are included will depend on a number of factors, e.g., on the end use of the sensor, the materials involved in the "sensing chemistry," and the like. The configuration of the inner adhesive layer controls the geometry of the sensing layer applied thereto, and can be manipulated to obtain optimum sensor signal strengths and adhesion. It allows sensors to be manufactured in which there is excellent mechanical adhesion, but not necessarily covalent bonding, between the adhesive and sensing layers. The mechanical adhesion results from the deposition of the sensing layer directly on the inner adhesive material, the geometry of the sensing and adhesive layers, and the materials selected for these layers.

In another aspect of the invention, sensors are provided which are made by the aforementioned method. While these sensors can be used for a variety of purposes, depending on the materials incorporated into the layers provided on the fiber tip, they will primarily be used in the measurement of oxygen concentration, carbon dioxide concentration and pH in physiological fluids, particularly in blood.

BRIEF DESCRIPTION OF THE DRAWINGS

In the course of this description, reference will be made to the attached drawings, wherein.

DETAILED DESCRIPTION OF THE INVENTION

Definitions

Figure 1:
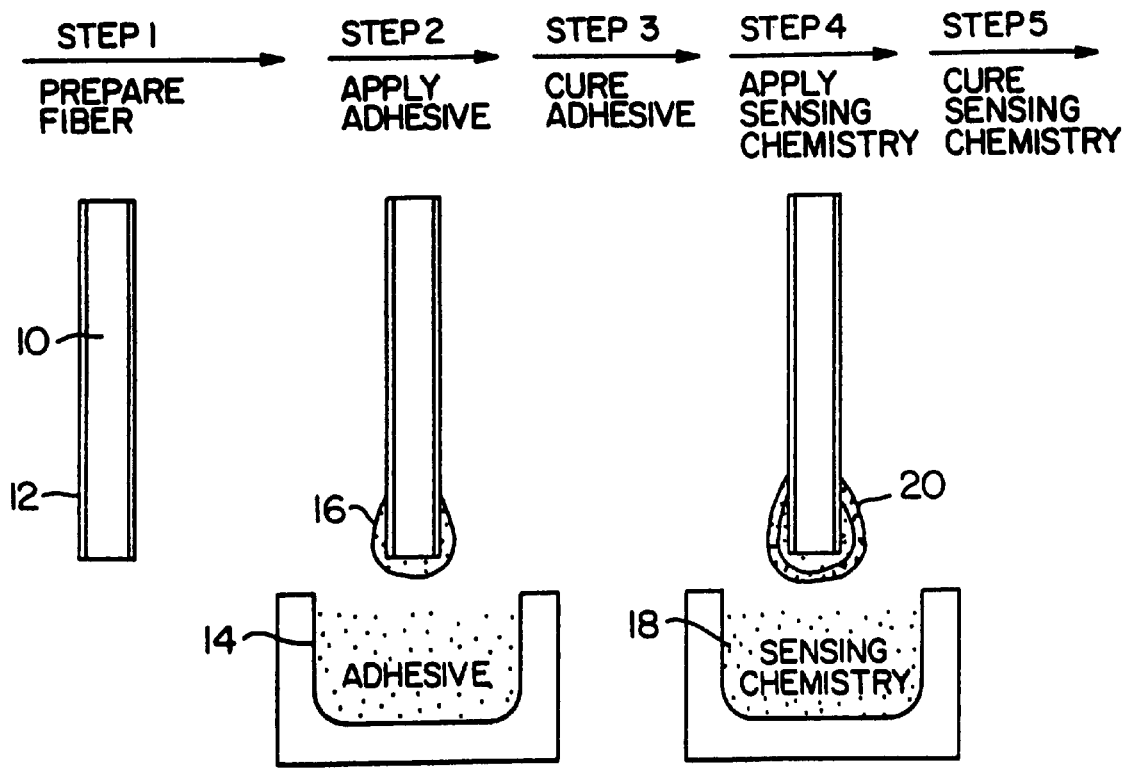
FIG. 1 is a schematic view of one method of manufacturing a sensor device according to the present invention.

Before the present sensors and methods are disclosed and described, it is to be understood that this invention is not limited to specific sensor formats, specific indicator compositions, or particular adhesives, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an indicator material" includes mixtures of suitable indicator materials, reference to "an adhesive material" includes mixtures of two or more adhesives, reference to "an adhesive layer" or "an inner adhesive layer" includes two or more adhesive layers, reference to "a sensing layer" or "an outer sensing layer" includes two or more sensing layers, and the like.

In describing and claiming the present invention, the following terminology will be used in accordance with the definitions set out below.

The term "optical fiber means" is used herein to refer to a single optical fiber or a bundle optical fibers. Suitable materials for optical fibers will be outlined below.

The term "sample fluid" as used herein refers to a liquid or gaseous material which may be analyzed using the presently disclosed sensors, either with respect to a parameter such as pH, or with regard to the presence or concentration of gases such as oxygen, carbon dioxide, or the like. Generally, "sample fluids" analyzed using the sensors manufactured herein will be physiological fluids such as blood.

The term "indicator" as in "indicator composition," "indicator material" or "indicator component" refers to a species which is sensitive to a parameter of interest in the sample undergoing analysis. For example, an oxygen indicator will generally be an organic and/or organometallic chemical compound which, when exposed to an appropriate wavelength of light, emits a measurable fluorescence signal which is sensitive to (i.e., quenched by) the oxygen to which it is exposed. For measuring pH, the indicator will generally be a fluorescent dye or some other fluorescent material which is pH-sensitive.

The terms "reference material" or "reference dye" intends a species which is substantially insensitive to the parameter of interest in the sample undergoing analysis, and will be used in conjunction with an indicator material. For example, reference dyes used in conjunction with oxygen sensors will typically be chemical compounds which, when exposed to a particular wavelength of light, emits a measurable fluorescence signal which is substantially insensitive to (i.e., not significantly quenched by) oxygen.

The term "sensing chemistry" as used herein refers to a composition containing components which in combination enable measurement of the parameter of interest in a sample fluid. For example, "pH sensing chemistry" intends a composition containing chemical components which enable measurement of pH, while "oxygen sensing chemistry" intends a composition containing chemical components which enable measurement of $pO_2$.

The term "polymer" as used herein is intended to include both oligomeric and polymeric materials, i.e., compounds which include two or more monomeric units. The term is also intended to include "copolymeric" materials, i.e., containing two or more different monomeric units. Similarly, the term "perfluorinated polyether" linkage is intended to mean a linkage containing at least two perfluorinated ether mer units, i.e., ether mer units in which each hydrogen atom normally present has been replaced by a fluorine atom.

The term "urethane" is used herein in its conventional sense to denote organic compounds containing a recurring —O—(CO)—NH— linkage. The term "urethane acrylate polymer" is intended to mean a urethane polymer derived from polymerization of a urethane oligomer having acrylate or acrylamide termini —(CO)—R—CR'=$CH_2$ wherein R is NH or O and R' is hydrogen or lower alkyl. The term "polyether-containing urethane" is intended to mean a polymer containing recurring urethane units as just defined, as well as recurring ether linkages [—($CH_2$)$_n$—O—] where n is an integer greater than 1, typically in the range of 1 to 6 inclusive, most typically 1, 2 or 3.

The term "precursor" is used herein to mean a compound which when polymerized and/or cross-linked will give rise to a desired polymer. For example, the term "perfluorinated urethane polymer precursor" denotes a compound which when treated with, for example, moisture, radiation, cross-linking agents, or combinations thereof, will give rise to a "perfluorinated urethane polymer" as will be described in greater detail below.

In describing chemical compounds herein, the term "lower alkyl" is used in its conventional sense to mean an alkyl group of 1 to 6 carbon atoms, e.g., methyl, ethyl, n-propyl, isopropyl, n-butyl, isobutyl, t-butyl, and the like. "Lower alkylene" refers to a difunctional saturated branched or unbranched hydrocarbon chain containing from 1 to 6 carbon atoms, and includes, for example, methylene (—$CH_2$—), ethylene (—$CH_2CH_2$—), propylene (—$CH_2$—$CH_2$—$CH_2$—), and the like. The term "alkylarylene" refers to a difunctional hydrocarbon moiety containing 1 or 2 monocyclic aromatic moieties, either unsubstituted phenyl rings or containing one to four substituents such as lower alkyl, halogen, nitro, or the like. "Alkylarylene" linking groups may also contain lower alkylene spacers adjacent the aromatic rings, in which some or all of the hydrogen atoms normally present may be replaced with fluorine atoms.

The term "olefin" is used in its conventional sense to mean a molecular entity containing a double bond; preferred olefinic species are molecular entities containing at least one terminus represented by the general formula —(CO)—R—CR'=$CH_2$, wherein R is NH or O, and R' is hydrogen or lower alkyl.

Overview of the Inventive Method

As will be explained in detail below, the invention involves deposition of two or more layers on the tip of an optical fiber; it is the composition of these layers which enables measurement of a parameter of interest in a sample. At the outset, an optical fiber means is provided which serves to communicate optical signals from a sample fluid to a detection means. The optical fiber means will typically comprise a single elongated optical fiber, although it may comprise a bundle of optical fibers associated in parallel.

Examples of suitable fiber substrate materials include glass, plastic, glass/glass composite and glass/plastic composite fiber waveguides. A critical characteristic of optical fibers is attenuation of the optical signal. Thus, glasses which contain unacceptable levels of transition-metal impurities when prepared from naturally occurring materials lead to high absorption losses. Silica fibers of acceptable quality can be prepared from purified starting materials (e.g., silicon tetrachloride and germanium tetrachloride) using conventional glass-melting techniques of drawing into fibers.

Generally, although not necessarily, the fiber will be provided with a cladding means. As will be appreciated by those skilled in the art, the cladding means serves to provide structural support for an otherwise fragile fiber, and also provides a coating which guides light conducted along the fiber. In the present case, the cladding means typically comprises a fluoropolymer such as polymeric fluoroacrylate. However, the cladding means may also be comprised of glass, or it may be comprised of polystyrene, polyimide or any other suitable plastic material.

Prior to deposition of the adhesive layer, the fiber tip region may, if desired, be pretreated, for example, by rinsing or washing, or by activation using any number of techniques (e.g., corona, plasma, etching, or the like). Other surface treatment methods may also be used if desired; generally such methods will be selected so as to enhance the adhesion of the innermost layer.

The innermost layer is deposited on the tip of the fiber typically using a simple dip coating procedure. This layer comprises an adhesive material, preferably a photocurable adhesive material. A wide variety of adhesive materials can be used, so long as sufficient adhesion is provided between the fiber or cladding material and the layer or layers containing the sensing chemistry. It is also necessary that the materials of the innermost layer be physically and chemically compatible with other materials used to construct the sensor and, clearly, with any other components incorporated into the innermost layer itself, e.g., reference dyes or the like.

Examples of preferred adhesive materials include, but are not limited to, polyurethanes, polyurethane precursors, acrylated polyurethanes, acrylated polyurethane precursors, acrylates, epoxy resins, acrylated epoxy resins, and silicones, with urethane-based and urethane acrylate adhesives particularly preferred. Radiation curable materials are generally preferred as well, as noted above, although materials which may be cured using alternative techniques may also be used, e.g., moisture-curable or heat-curable adhesives.

Examples of specific commercially available adhesives which can be used to prepare the innermost layer herein include the following: the urethane-based adhesives Airthane®, Polathane®, Ultracast® and Cyanaprene® (Air Products and Chemicals, Inc.), as well as Conathane®

(Conap, Inc.), Rubinate® (ICI Polyurethanes Group), and Jedbond® (Jedco Chemical Corp.); radiation-curable aliphatic and aromatic urethane acrylates and epoxy acrylates available from Sartomer Co., Inc. under the tradenames CN 950, 960, 970, 980, 104, 111, 114 and 120; urethane acrylates available under the trademark Purelast® from Polymer Systems Corp.; urethane acrylates 3321, 3311, 3211 and 3301 available from Loctite; acrylate and methacrylate epoxies and urethanes available from Echo, Inc.; and epoxy and urethane acrylates available from Cargill, Inc., and the radiation-curable acrylic resins available under the trademarks Tritherm®, Terasod®, Pedigree® and Soderite® from the P. D. George Co.

Other components may be incorporated into the adhesive layer as well, typically any materials that are compatible with the adhesive, the components of the outer, sensing layer or layers, and the fiber or cladding material. The adhesive layer may, for example, contain a cross-linking agent to facilitate curing. Alternatively, or in addition, the adhesive layer can be used to incorporate one of two dye materials used in analyte measurement. When two dyes are used in a particular type of measurement, e.g., a species-sensitive indicator material and a species-insensitive reference dye, it may be desirable to incorporate the reference dye into the innermost layer to enhance signals and/or minimize contact with analyte.

It may also be desired to deposit two or more adhesive layers rather than a single adhesive layer. In this manner, additional surface area can be generated to which the sensing layer or layers can bind, in turn enabling mechanical adhesion around the rounded sides of the adhesive layer on the cladding and more indicator to be present at the fiber tip. The presence of additional indicator will enhance the signal obtained in response to any given measurement.

It may be desirable to mold or form the inner adhesive layer prior to curing, to change the geometry of the tip, again, typically to optimize the surface area to which additional layers bind. In this way, as with the use of multiple adhesive layers, it becomes possible to mechanically bind the sensing layer or layers to the fiber tip.

Generally, the thickness of the adhesive present at the fiber optic tip will be in the range of about 15 to about 200 microns.

The adhesive layer is then partially or fully cured, using moisture, heat, or, preferably, ultraviolet radiation (alternatively, curing may, in some cases, occur simply with the passage of time). With ultraviolet curing, the coated tip is exposed to radiation of a predetermined wavelength, and for a time and at an intensity selected to effect the desired degree of curing. The coated tip is preferably exposed to ultraviolet light in a uniform manner, and preferably from an external source rather than through the fiber. It may in some cases be desirable to cure the innermost layer only partially, such that a reactive surface is provided, in turn enabling covalent binding of the next layer of material. With a fully cured innermost layer, the next layer will adhere mechanically rather than chemically; with a partially cured innermost layer, adhesion of the next layer may be both chemical and mechanical.

After the innermost layer is provided on the fiber tip, formed into a desired geometry, and partially or fully cured, additional adhesive layers may be provided, followed by deposition of a subsequent layer. The contains the "sensing" materials necessary to conduct the desired measurement, e.g., of pH, blood gas concentration, or the like. Additional sensing layers may, if desired, be present.

FIG. 1 illustrates in schematic form the methodology of the invention. The fiber is shown at element 10 with cladding 12 present thereon. In step (1), the fiber is prepared, by rinsing or other treatment as described above. In step (2), the adhesive solution 14 is applied to the fiber tip, giving rise to innermost layer 16. This inner adhesive layer 16 controls the geometry of the sensing layer and is an important element in optimizing sensor adhesion and signal strength. As noted earlier herein, the shape and thickness of the layer can be manipulated via the application parameters to yield the desired geometry. In step (3), the innermost layer is cured, followed by preparation of sensing chemistry 18 and application thereof, in step (4), to provide sensing layer 20. In step (5), the outer layer comprising the sensing chemistry is cured. In an alternative method, the sensing layer may first be cast as a film, and then adhered to the fiber tip.

Figure 2:
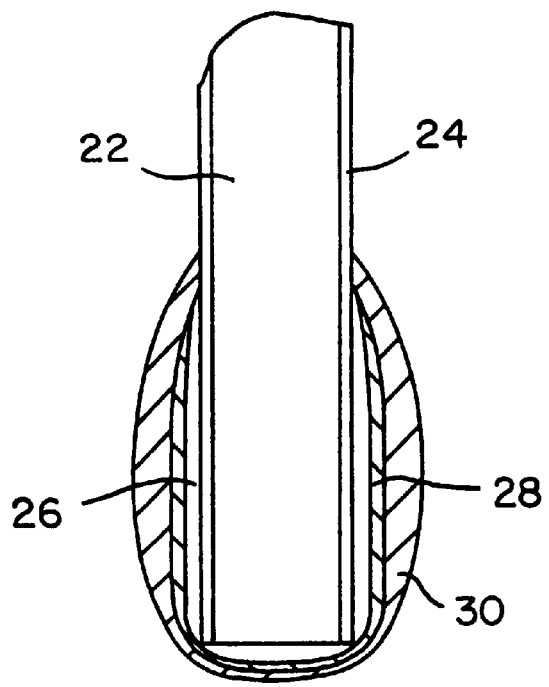
FIGS. 2, 3, 4 and 5 represent in schematic form various configurations of sensors manufactured using the techniques of the present invention.
Figure 3:
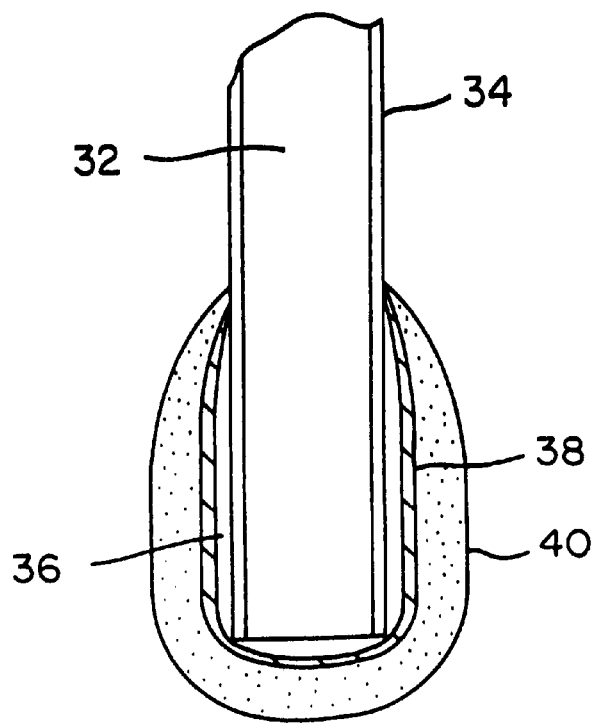

FIGS. 2 through 5 illustrate in schematic form various configurations of sensors which may be manufactured using the presently disclosed and claimed techniques. In FIG. 2, the fiber 22 is shown as having a cladding 24 present thereon, innermost adhesive layer 26 deposited thereon, with two sensing layers 28 and 30 overlying the adhesive material. In FIG. 3, the fiber is shown as element 32, with cladding material present thereon at 34, inner adhesive layer 36 and sensing layer 38. Element 40 represents an analyte-selective outer layer comprised of a polymeric material, which is generally although not necessarily present in carbon dioxide sensors, as will be explained below.

Figure 4:
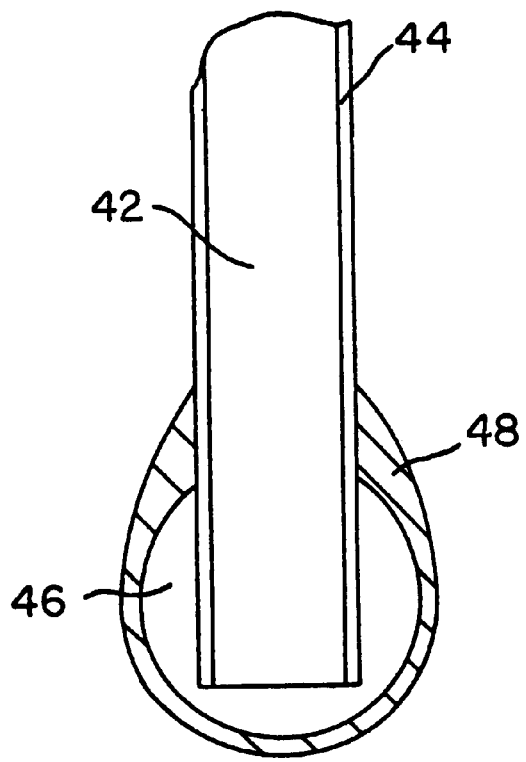
Figure 5:
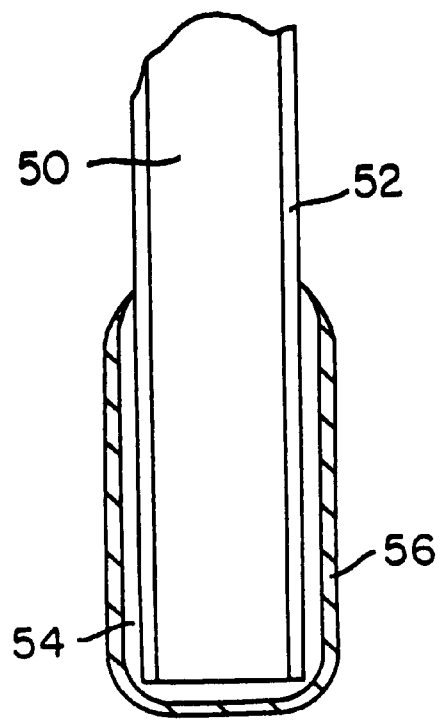

In FIG. 4, a sensor is shown substantially as prepared in the scheme of FIG. 1, with the fiber shown as element 42 having cladding present thereon at 44, a rounded inner adhesive layer deposited around the fiber tip region and represented as 46, and a thin layer 48 of sensing chemistry deposited thereover. FIG. 5 is substantially the same sensor, with the fiber present as element 50 having cladding 52 thereon, although in this case the adhesive has been formed into a relatively thin layer 54 which is less rounded than in the configuration of FIG. 4, and having sensing layer 56 deposited thereon.

pH Sensors

For use as a pH sensor, the sensing layer will contain the "sensing chemistry" necessary for the device to be used in measuring pH. Generally, although not necessarily, the initial sensing layer will serve as an intermediate layer, with an additional sensing layer present which has a chemical composition identical to that of the initial sensing layer. The components of these layers will be selected so as to enable measurement of pH in a sample fluid; preferred components are those described in commonly assigned U.S. Pat. No. 5,607,644 to Olstein et al. the disclosure of which is incorporated by reference in its entirety. For purposes of completeness, the following is a brief description of the sensing chemistry described in the aforementioned document.

For measurement of pH, the sensing layer or layers will be formulated from a fluorescent polymer composition comprising a hydrophilic, fluorescent polymer, preferably although not necessarily a copolymer of (a) a hydrophilic, polyether-containing urethane olefin precursor, and (b) a monomeric fluorescent indicator species, with the ratio of urethane olefin precursor to the fluorescent species calculated to provide the composition with a pKa in the range of approximately 6.6 to 8.0, preferably in the range of about 7.2 to 7.8, and most preferably in the range of about 7.2 to 7.4. This in turn optimizes the composition for use in measuring pH in the physiological range.

The preferred molecular weight of the copolymer is in the range of approximately 1000 to 25,000, more preferably in the range of approximately 1800 to 5000, and most preferably in the range of approximately 1800 to 2500. The urethane olefin precursor contains recurring urethane units, recurring ether linkages, and olefinic termini represented by the general formula —R—(CO)—CR'=CH$_2$, wherein R and R' are as defined earlier, i.e., R is NH or O and R' is hydrogen or lower alkyl; it should also be noted that the R and R' at the different termini are not necessarily the same (i.e., R may be O at one terminus and NH at the other, and, similarly, R' may be H at one terminus and CH$_3$ at another). Preferred urethane olefin precursors are represented by the general structural formula

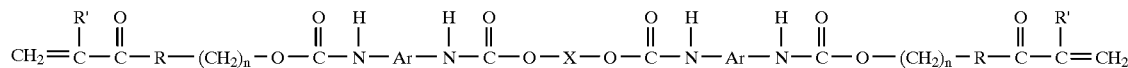

wherein: R and R' are as defined previously; n is typically in the range of 1 to about 6; Ar is a monocyclic aromatic moiety, preferably phenyl, either unsubstituted or substituted with one to four substituents which are selected so as not to interfere with polymerization or use of the cured polymer in the pH sensor, e.g., lower alkyl, halogen, nitro and the like; and X is a polyether linkage containing approximately 2 to 100, preferably 10 to 50, most preferably 15 to 25, recurring mer units having the structure [—(CH$_2$)$_n$—O—] where n is an integer of 1 or more, typically 1 to 6, more typically 2 or 3, i.e., (—CH$_2$—CH$_2$—O—), (—CH$_2$—CH$_2$—CH$_2$—O—), or combinations thereof. These polyether linkages may be further substituted with an additional —CO—NH—Ar—NH—CO$_2$—(CH$_2$)$_n$—R—(CO)—CR'=CH$_2$ group to provide a trifunctional urethane olefin precursor. Methods for synthesizing urethane olefin precursors are described in detail in commonly assigned U.S. Pat. No. 5,453,248 to Olstein, the disclosure of which is hereby incorporated by reference. Briefly, that method involves conversion of isocyanate-terminated compounds represented by the general formula

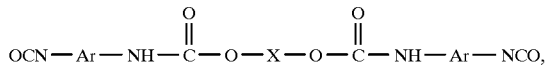

wherein X is as defined above, to urethane olefin precursors by replacing the terminal isocyanate moieties with olefin termini. The isocyanate-terminated starting material is reacted with the desired olefin monomer or oligomer, i.e., a hydroxy- or amine-terminated acrylate, methacrylate, acrylamide, methacrylamide, e.g., hydroxyethylmethacrylate (in which case n=2). Urethane precursors such as Hypol® 2000 are commercially available from Hampshire (Lexington, Mass.). Urethane olefin precursors such as Hypol® 2000 such as 9454, 9455, 9734 and 9467, and RCC-12-893, Photomers 6230 and 6264 are commercially available from Monomer-Polymer and Dajec Laboratories, Inc. (Trevose, Pa.) and Henkel Corporation (Ambler, Pa.), respectively.

The copolymerizable fluorescent monomer species may be virtually any fluorescent dye or material which is sensitive to pH, modified so as to enable copolymerization with the urethane olefin precursor. Exemplary preferred modifications include incorporation into the fluorescent monomer species of a reactive moiety such as acrylate, acrylamide, allyl esters, allyl amides, and the like, such that the fluorescent species is thereby incorporated into the backbone of the polymer chain. Examples of fluorescent monomer species useful herein include fluorescein and fluorescein derivatives such as carboxyfluorescein, fluorescein acrylamide, fluorescein isothiocyanate, coumarin, seminaphthorhodafluorescein, seminaphthofluorescein, naphthofluorescein, hydroxypyrene trisulfonic acid and dichlorofluorescein, and the like, again, bearing a reactive site effective to promote incorporation into the copolymer.

The coating solution to provide the sensing layer in the pH sensors is prepared by admixing the urethane olefin precursor and the fluorescent monomer species, along with a photoinitiator in a suitable solvent. The total amount of the dissolved solids is typically in the range of about 50% to 90% by weight. Generally, the coating solution will contain on the order of 50 to 90 g urethane olefin precursor, 1×10$^{-3}$ to 0.5 g photoinitiator, and 0.05 to 5 g fluorescent monomer per 100 g solution. Preferred solvents include water-miscible, low boiling point solvents such as methanol and ethanol, and partially water-miscible solvents such as ethyl acetate. Water-miscible, polar solvents that have higher boiling points may also be used, such as dimethylsulfoxide, dimethylformamide, N-methyl-pyrrolidone, dimethylacetamide, or the like. A preferred high boiling point solvent is dimethylsulfoxide used at about 10% to 50% by weight.

A suitable cross-linking agent may be added, particularly any di- or multifunctional acrylate. Examples of such cross-linking agents include

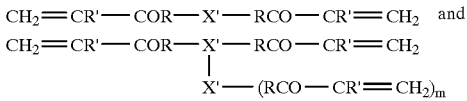

wherein R and R' are as defined above, m is 1, 2 or 3, and X' is a polyether substituent as defined above or a hydrocarbon, preferably alkylene, group containing about 2 to 20 carbon atoms.

Suitable photoinitiators are radical photoinitiators that are well known to those skilled in the art. Examples of such photoinitiators include α-alkoxy deoxybenzoins, α,α-dialkoxy deoxybenzoins, α,α-dialkoxy acetophenones, 2-hydroxy-2,2-dialkyl acetophenones, benzophenones, thioxanthones, benzils, and other compounds identified by H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53, cited supra. The disclosure of the aforementioned reference is incorporated by reference herein.

The pH sensing chemistry in the sensing layer also, preferably, includes particulate titanium dioxide to increase the signal obtained. Generally about 1% to 10% by weight titanium dioxide is dispersed uniformly throughout the polymeric composition prior to application to the fiber tip.

The composition used to form the outer, sensing layer of the present pH sensors will generally include: 50 to 90 wt. % polymer; 0.05 to 1.0 wt. % fluorescent monomer; and 0.05 to 1.0 wt. % photoinitiator, with the remainder of the sensing layer comprising an appropriate solvent.

The aforementioned embodiment, relating to the use of a fluorescent copolymer in the inner adhesive, as described in co-pending application Ser. No. 08/074,749, now U.S. Pat. No. 5,607,644 is generally preferred. However, it will be appreciated by those skilled in the art that the present methodology extends to other types of indicator-containing compositions as well, e.g., wherein fluorescent dyes or other types of indicator materials are entrapped in or ionically bound to a polymer matrix (such as an ion exchange resin).

The fiber tip, having the inner adhesive layer already present, is then coated with the aforementioned solution, typically using a similar dip coating technique used to provide the adhesive, so as to give rise to an outer layer containing the sensing chemistry. Curing is then conducted as described with respect to the adhesive layer, using ultraviolet radiation of a predetermined wavelength and intensity.

After the initial sensing layer is provided, it is then preferred, although not essential, to provide a further sensing layer, identical to the initial layer, using the same methodology. Each of the sensing layers will generally be in the range of about 10 to about 50 microns in thickness.

The composition used to form the outer, sensing layer of the present oxygen sensors will generally include: 80 to 99 wt. % polymer; 0.05 to 1.0 wt. % fluorescent monomer; and 0.05 to 1.0 wt. % photoinitiator, with the remainder of the sensing layer comprising an appropriate solvent. The innermost layer of the oxygen sensors will generally comprise 95 to 100 wt. % adhesive and 0.05 to 1.0 wt. % reference dye, with the remainder of the adhesive layer comprising an appropriate solvent.

Once prepared, with the layers described above having been cured, the pH sensor is then stored in a saline solution in order to hydrate the sensor coating prior to use.

Oxygen Sensors

For oxygen sensors, the sensing layer will typically serve as the sole outer layer, and will contain components useful for measuring oxygen concentration. While any composition may be used for the sensing layer so the components contained therein enable measurement of $pO_2$, it is preferred that the chemistry be that described in applicants' co-pending, commonly assigned U.S. patent application Ser. No. 07/911,175, incorporated by reference above.

For measurement of $pO_2$, the sensing layer will preferably be formed from a composition comprising a matrix of a cured perfluorinated urethane polymer; preferably, the perfluorinated urethane polymer is a perfluorinated polyurethane acrylate formed by cross-linking a perfluorinated polyurethane acrylate precursor with a cross-linking agent. These precursors generally have the structural formula (I)

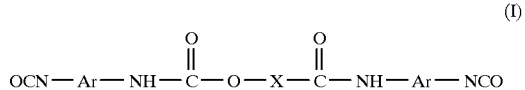

wherein Ar is a monocyclic aromatic moiety and X is a perfluorinated polyether linkage containing approximately 2 to 100, preferably 10 to 50, most preferably 15 to 25, recurring perfluorinated mer units having the structure $-(CF_2O)-$, $-(CF_2CF_2O)-$, or combinations thereof.

Preferably, Ar is phenyl, either unsubstituted or substituted with one to four substituents which are selected so as not to interfere with polymerization or use of the cured polymer in the sensor; such substituents include, for example, lower alkyl ($C_1-C_6$), halogen, nitro, and the like.

The precursor of Formula (I) may be crosslinked using water or an organic diol HO—$R^1$—OH wherein $R^1$ is a hydrocarbon substituent of about 2 to 20 carbon atoms, and in which some or all of the hydrogen atoms normally present have been replaced with fluorine atoms. Preferably, $R^1$ is an alkylene linking group, i.e., an alkylene linking group containing from about 1 to 6 carbon atoms, or an alkylarylene linking group containing one or two monocyclic aromatic moieties and, depending on the number of aromatic moieties, two or three lower alkylene spacer groups, again, in which some or all of the hydrogen atoms normally present have been replaced with fluorine atoms. Exemplary organic diols include bisphenol A and hexafluorobisphenol A.

In a preferred embodiment, the precursor of Formula (I) is converted to a perfluorinated urethane acrylate precursor prior to curing, by replacing the terminal isocyanate moieties —N=C=O with acrylate termini —NH—COO—$(CH_2)_n$—(CO)—CH=$CH_2$ where n is typically in the range of 1 to about 6. This may be effected by reacting the diisocyanate precursor (I) with, for example, hydroxymethylmethacrylate (in which case n is 1), hydroxyethylmethacrylate (in which case n is 2), or the like. The perfluorinated urethane acrylate precursor so provided has the structural formula

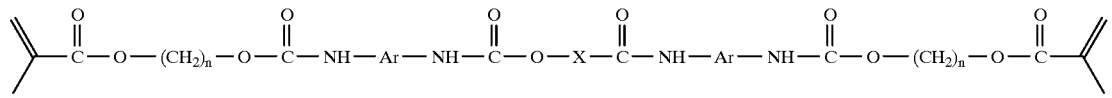

In a variation on this embodiment, the diisocyanate-terminated precursor of Formula (I) may be reacted with virtually any compound having a hydroxy terminus and a vinyl terminus, typically containing about 2 to 10 carbon atoms, to provide a vinyl-terminated precursor and to enable cross-linking.

Suitable photoinitiators for carrying out the cross-linking in the aforementioned case, i.e., to cure the perfluorinated urethane acrylate precursor of Formula (II), are radical photoinitiators as described above with respect to pH sensors that may be fabricated using the inventive techniques, i.e., α-alkoxy deoxybenzoins, α,α-dialkoxy deoxybenzoins, α,α-dialkoxy acetophenones, and the like. When the sensing chemistry is based on perfluorinated urethane acrylate precursors having the structure of formula (II), then, the sensing layer will include not only those precursors but also a photoinitiator as just described.

In another embodiment, the diisocyanate-terminated precursor of Formula (I) is converted to an epoxy-terminated precursor having the formula

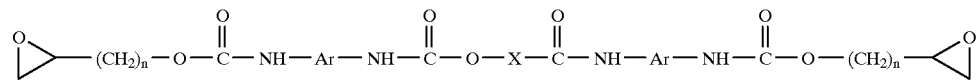

wherein Ar, X, and n are as defined above. This conversion may be readily effected by reaction of the precursor of Formula (I) with two equivalents of a compound having the structural formula

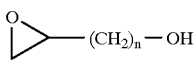

(i.e., glycidol when n is 1). In this case, also, it will be necessary to include a suitable photoinitiator in the oxygen sensing chemistry. Suitable photoinitiators in this case are cationic photoinitiators, e.g., sulfonium salts, or organometallic complexes such as that manufactured under the name Irgacure® by Ciba-Geigy Corporation, or the like.

The sensing layer of the oxygen sensor also includes an indicator component which is incorporated into the polymeric matrix described above. The indicator will generally be physically entrapped within the polymeric matrix, but it may also be covalently bound thereto. The indicator is typically an organometallic or inorganic complex which is a luminescent material quenchable by oxygen. Examples of suitable gas-sensitive indicators useful for $O_2$ determination include complexes of ruthenium (II), osmium (II), iridium (III), rhodium, rhenium, and chromium (III) with 2,2'-bipyridine, 1,10-phenanthroline, 4,7-diphenyl(1,10-phenanthroline), 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, and 5-chloro-1,10-phenanthroline, and complexes of VO (II), Cu (II), platinum (II), and zinc (II) with etioporphyrin, tetraphenylporphyrin, mesoporphyrin IX dimethylester, protoporphyrin IX dimethylester and octaethylporphyrin. Preferred gas-sensitive indicators for fabricating oxygen sensors are ruthenium complexes.

With oxygen sensors, it is preferred that a reference dye be used as well, but incorporated in the innermost layer rather than in the outer layer, to enhance signals and/or minimize contact with analyte. As explained in applicants' co-pending, commonly assigned U.S. patent application Ser. No. 08/120,593, now U.S. Pat. No. 5,462,880, entitled "A Ratiometric Fluorescence Method to Measure Oxygen," the disclosure of which is incorporated by reference herein, suitable reference dyes are typically organic luminescent materials which are relatively unquenchable by oxygen (i.e., have a Stern Volmer constant $K_{sv}$ which is substantially smaller than that of the oxygen-sensitive indicator; in general, the $K_{sv}$ of the reference dye should be at least 0.05 less than that for the oxygen-sensitive indicator), have a fluorescence emission spectrum which can be readily discerned from that of the oxygen indicator dye and have a relatively stable photodrift rate that is closely matched to that of the oxygen-sensitive indicator. Examples of reference dyes include polynuclear aromatic compounds, such as perylene derivatives, fluorescein and fluorescein derivatives such as carboxyfluorescein, hydroxypyrene trisulfonic acid, dichlorofluorescein, and the like. Preferred examples of such reference dyes are N,N'-bis(2,5-di-tertbutylphenyl)-3,4,9,10-perylenebis(dicarboximide) and N,N'-bis(2,6-xylidyl)-3,4,9,10-perylenebis(dicarboximide) (DXP).

The oxygen sensing chemistry in the sensing layer also, preferably, includes particulate titanium dioxide to increase the signal obtained. As with the pH sensors described earlier, the titanium dioxide is preferably dispersed uniformly throughout the polymeric composition prior to application to the fiber tip. As above, titanium dioxide is generally included in an amount between about 1 to 10 wt. % relative to the total composition of the sensing layer.

The oxygen sensing layer is provided typically by using a simple dip coating method as set forth above, i.e., by immersing the fiber having the adhesive layer already present and cured, in a composition containing the aforementioned components. Generally, the coating composition will be maintained at an elevated temperature, typically on the order of 45° C. or greater, which is controlled to maintain the optimum geometry. Curing is again conducted by exposure to ultraviolet radiation of a predetermined wavelength. If desired, additional sensing layers can be deposited using the same technique.

Once prepared, with the layers described above having been cured, the $pO_2$ sensor thus formed is then stored in a saline solution.

Carbon Dioxide Sensors

The present methodology may also be extended to encompass preparation of fiber optic sensors used to measure $pCO_2$. The same manufacturing techniques are used as described above with respect to pH and oxygen sensors, i.e., an inner adhesive layer is applied to the distal end of an optical fiber, and a sensing layer is deposited thereon containing an indicator composition.

In preferred carbon dioxide sensors, the indicator composition comprises a fluorescent dye which is associated with a hydrophilic polymer (that is, either entrapped within or covalently bonded to such a polymer). Suitable fluorescent dyes are generally but not necessarily selected from the group consisting of fluorescein, carboxyfluorescein, fluorescein acrylamide, fluorescein isothiocyanate, coumarin, seminaphtharhodafluorescein, seminaphthafluorescein, naphthafluorescein, hydroxypyrene trisulfonic acid and dichlorofluorescein.

The adhesive layer, the sensing layer, or both, may also include a reference dye substantially insensitive to the concentration of carbon dioxide in the sample fluid undergoing analysis.

Carbon dioxide sensors prepared using the present techniques preferably have an additional layer deposited on the outer layer, comprised of an analyte-selective polymeric material such as a silicone or a fluoropolymer.

It will be appreciated by those working in the art that sensors fabricated using the presently disclosed and claimed techniques may be used in a wide variety of contexts, including glucose determination, measurement of potassium ions, calcium ions, magnesium ions, and the like. Also, while the invention has primarily been described in conjunction with the measurement of analytes in blood, the sensors fabricated using the present method may be used to evaluate a wide range of parameters in any number of sample types.

Thus, it is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

Experimental

The following examples are put forth so as to provide those of ordinary skill in the art with a complete disclosure and description of how to make and use the compounds of the invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All solvents were purchased as HPLC grade and, where appropriate, solvents and reagents were analyzed for purity using common techniques.

Reagents were obtained as follows: Hypol® 2000 polyurethane prepolymer, from Hampshire (Lexington, Mass.); hydroxypropyl methacrylamide and hydroxyethyl methacrylate, from Polysciences, Inc. (Warrington, Pa.); methyl sulfoxide, from Aldrich (Milwaukee, Wis.); Darocur® 1173 and Irgacure® 500, from Ciba-Geigy (Hawthorne, N.Y.); Fluorolink® B perfluorinated polyurethane prepolymer, from Ausimont (Morristown, N.J.); tris (4,7-diphenyl-1,10-phenanthroline) ruthenium (II), from GFS Chemicals (Columbus, Ohio); adhesives 3321 and 3211, from Loctite (Newington, Conn.); and N,N'-bis(2,6-xylidyl)-3,4,9,10-perylenebis(dicarboximide) was prepared according to H. Langhals, *Chem. Ber.* 118:4641 (1985), with substitution of 2,6-dimethylanailine from Aldrich (Milwaukee, Wis.) for 2,5-di-tert-butylaniline in reaction with 3,4,9,10-perylenetetracarboxylic dianhydride (Aldrich).

EXAMPLE 1

Preparation and Evaluation of a pH Sensor

The objective of this example was to prepare a pH sensor having a cured inner layer of an acrylated urethane adhesive, and an outer layer containing pH sensing chemistry.

The fiber used was Spectran Specialty optic's (Avon, Conn.) HCN/H High NA HCS containing pure silica core bonded to a hard polymer cladding. The fiber was pretreated by washing with ethanol followed by air drying. Loctite adhesive 3211 was placed in a well. The fiber was placed into a holder and lowered into the adhesive in order to coat the tip. The fiber was raised from the adhesive well and the adhesive-coated fiber was cured under nitrogen with an Oriel mercury arc lamp.

A solution of pH sensing chemistry was prepared containing the following components: polyurethane methacrylamide prepolymer (prepared by reaction of Hypol® 2000 polyurethane prepolymer with hydroxypropyl methacrylamide), 1 g of 75 wt. % in methyl sulfoxide; fluorescein acrylamide, 1.2 mg in 30 μL ethanol; and Darocur 1173, 3 μL.

The fiber having the cured adhesive inner layer was then placed into a holder and lowered into a well containing the pH sensing chemistry until the adhesive was completely covered. The fiber was raised from the pH chemistry well and curing was performed as listed above.

The cured fiber tip was then placed in a saline solution in order to hydrate the coating prior to use.

The pH sensor so prepared was then evaluated for pH responsiveness, stability toward steam sterilization (increased pressure and temperature challenge), and sample fluid shear forces. Sensing chemistries remain attached following steam sterilization and exposure to excessive shear forces without deterioration in performance.

EXAMPLE 2

Preparation and Evaluation of a pH Sensor Containing a Reflective Source

The objective of this example was to prepare a pH sensor having a cured inner layer of an acrylated urethane adhesive, and an outer layer containing pH sensing chemistry and a reflective source to enhance signal levels.

Sensors were prepared as in Example 1 with the inclusion of titanium dioxide (50 mg in 40 wt. % methyl sulfoxide) in the pH sensing chemistry. Resultant sensors were tested as above and demonstrated same results.

EXAMPLE 3

Preparation and Evaluation of an Oxygen Sensor

The objective of this example was to prepare an oxygen sensor having a cured inner layer of an acrylated urethane adhesive, and an outer layer containing oxygen sensing chemistry and reference dye substantially insensitive to oxygen.

The fiber used was Spectran Specialty Optic's (Avon, Conn.) HCN/H High NA HCS containing pure silica core bonded to a hard polymer cladding. The fiber was pretreated by washing with ethanol followed by air drying.

Loctite adhesive 3321 was placed in a well. The fiber was placed into a holder and lowered into the adhesive in order to coat the tip. The fiber was raised from the adhesive well and the adhesive-coated fiber was cured under nitrogen with an Oriel mercury arc lamp.

A solution of oxygen sensing chemistry and reference dye was prepared containing the following components; perfluorinated polyurethane mathacrylate prepolymer (prepared by reaction of Fluorolink B perfluorinated polyurethane prepolymer with hydroxyethyl methacrylate), 3 g; tris(4,7-diphenyl-1,10-phenanthroline) ruthenium(II), 9.0 mg in 800 μL methylene chloride; N,N'-bis(2,6-xylidyl)-3,4,9,10-perylenebis(dicarboximide), 0.92 mg in 400 μL methylene chloride; and Irgacure® 500, 36 μL. Methylene chloride was removed with vacuum to yield a 92–100% solids preparation.

The fiber having the cured adhesive inner layer was then placed into a holder and lowered into a well containing the oxygen sensing chemistry until the adhesive was completely covered. The fiber was raised from the oxygen chemistry well and curing was performed as listed above.

The cured fiber tip was then placed in a saline storage solution.

The oxygen sensor so prepared was then evaluated for oxygen responsiveness stability toward steam sterilization (increased pressure and temperature challenge), and sample fluid shear forces. Sensing chemistries remained attached following steam sterilization and exposure to excessive shear forces without deterioration in performance.

EXAMPLE 4

Preparation and Evaluation of an Oxygen Sensor with Partitioned Reference Dye The objective of this example was to prepare an oxygen sensor having a cured inner layer of an acrylated urethane adhesive containing reference dye substantially insensitive to oxygen, and an outer layer containing oxygen sensing chemistry.

The fiber used was Spectran Specialty Optic's (Avon, Conn.) HCN/H High NA HCS containing pure silica core bonded to a hard polymer cladding. The fiber was pretreated by washing with ethanol followed by air drying. Reference dye (N,N'-bis(2,6-xylidyl)-3,4,9,10-perylenebis (dicarboximide)), 0.6 mg in 65 μL methylene chloride, was blended with Loctite adhesive 3321, 1 g, and placed in a well. Methylene chloride was removed with an air stream, prior to placing the aformenetioned mixture in the well, to yield a 92–100% solids preparation. The fiber was placed into a holder and lowered into the adhesive in order to coat the tip. The fiber was raised from the adhesive well and the adhesive-coated fiber was cured under nitrogen with an Oriel mercury arc lamp.

A solution of oxygen sensing chemistry was prepared containing the following components: perfluorinated polyurethane methacrylate prepolymer (prepared by reaction of Fluorolink B perfluorinated polyurethane prepolymer with hydroxyethyl mathacrylate), 3 g; tris(4,7-diphenyl-1,10-phenanthroline) ruthenium(II), 9.0 mg in 800 µL methylene chloride; Irgacure® 500, 36 µL. Methylene chloride was removed with vacuum to yield a 92–100% solids preparation.

The fiber having the cured adhesive inner layer was then placed into a holder and lowered into a well containing the oxygen sensing chemistry until the adhesive was completely covered. The fiber was raised from the oxygen chemistry well and curing was performed as listed above.

The cured fiber tip was then placed in a saline storage solution.

Resultant sensors were tested as above, yielding substantially the same results.

EXAMPLE 5

Preparation and Evaluation of an Oxygen Sensor Containing a Reflective Source

The objective of this example was to prepare an oxygen sensor having a cured inner layer of an acrylated urethane adhesive containing reference dye substantially insensitive to oxygen, and an outer layer containing oxygen sensing chemistry and a reflective source to enhance signal levels.

Sensors were prepared as in Examples 3 and 4 with the inclusion of titanium dioxide (0.15 g) in the oxygen sensing chemistry. Resultant sensors were tested as above and substantially the same results were obtained.

We claim:

1. A fiber optic sensor for detecting or measuring a parameter of interest in a sample fluid, comprising:

an optical fiber having a distal tip, a proximal section for receiving a signal from the distal tip and relaying the signal to a detection means, and an elongate light-conducting section present therebetween;

a cured adhesive material bonded directly to the surface of the optical fiber at its distal tip and completely surrounding said tip, wherein the adhesive material is present as a coating having a desired configuration and thickness; and a sensing layer directly laminated to and completely covering the adhesive material so as to conform to the configuration thereof, comprising an indicator composition containing an indicator component which is sensitive to a parameter of interest in the sample fluid and provides a signal related thereto.

2. The sensor of claim 1, wherein the elongate light-conducting section of the optical fiber is encased in a cladding means.

3. The sensor of claim 1, wherein the indicator composition is prepared so as to contain particulate titanium dioxide.

4. The sensor of claim 1, further including an outer layer of an analyte-selective polymeric material deposited on the sensing layer.

5. The sensor of claim 1, wherein the adhesive material comprises a single adhesive layer.

6. The sensor of claim 1, wherein the adhesive material is comprised of an acrylic adhesive.

7. The sensor of claim 6, wherein the acrylic adhesive comprises a urethane acrylate.

8. The sensor of claim 1, wherein the parameter of interest is pH and the indicator composition comprises a fluorescent polymeric composition comprising a copolymer of a hydrophilic, polyether-containing urethane olefin precursor and a copolymerizable, monomeric fluorescent indicator species.

9. The sensor of claim 8, wherein the fluorescent indicator species is selected from the group consisting of fluorescein, carboxyfluorescein, fluorescein acrylamide, fluorescein isothiocyanate, coumarin, seminaphthorhodafluorescein, seminaphthofluorescein, naphthofluorescein, hydroxypyrene trisulfonic acid and dichlorofluorescein, said species modified so as to enable copolymerization with the urethane olefin precursor.

10. The sensor of claim 1, wherein the adhesive material comprises a plurality of adhesive layers.

11. The sensor of claim 10, further including one or more additional indicator-containing layers deposited on the sensing layer.

12. The sensor of claim 1, wherein the parameter of interest is oxygen concentration and the indicator composition comprises a polymeric matrix of a cured perfluorinated urethane polymer, and, incorporated therein, an oxygen-sensitive indicator component.

13. The sensor of claim 12, wherein the indicator component is selected from the group consisting of complexes of ruthenium (II), osmium (II), iridium (III), rhodium, rhenium, and chromium (III) with 2,2'-bipyridine, 1,10-phenanthroline, 4,7-diphenyl-1,10-phenanthroline, 4,7-dimethyl-1,10-phenanthroline, 4,7-disulfonated-diphenyl-1,10-phenanthroline, 2,2'-bi-2-thiazoline, 2,2'-bithiazole, 5-bromo-1,10-phenanthroline, and 5-chloro-1,10-phenanthroline, and complexes of VO (II), Cu (II), platinum (II), and zinc (II) with porphyrin, etioporphyrin, tetraphenylporphyrin, mesoporphyrin IX dimethylester, protoporphyrin IX dimethylester and octaethylporphyrin.

14. The sensor of claim 12, further including one or more additional indicator-containing layers deposited on the sensing layer.

15. The sensor of claim 12, wherein the adhesive material contains a reference dye which provides a signal that is substantially independent of oxygen concentration, and wherein the sensing layer is such that sample fluid may permeate therethrough so as to contact the adhesive material.

16. The sensor of claim 15, wherein the reference dye is a fluorescent organic compound selected from the group consisting of fluorescein, carboxyfluorescein, hydroxypyrene trisulfonic acid, dichlorofluorescein, N,N'-bis(2,5-di-tert-butylphenyl)-3,4,9,10-perylenebis(dicarboximide), and N,N'-bis(2,6-xylidyl)-3,4,9,10-perylenebis(dicarboxmide).

17. The sensor of claim 12, wherein the sensing layer further contains a reference dye which provides a signal that is substantially independent of oxygen concentration, and wherein the sensing layer is such that sample fluid may permeate therethrough so as to contact the adhesive material.

18. The sensor of claim 17, wherein the reference dye is a fluorescent organic compound is selected from the group consisting of fluorescein, carboxyfluorescein, hydroxypyrene trisulfonic acid, dichlorofluorescein, N,N'-bis(2,5-di-tert-butylphenyl)-3,4,9,10-perylenebis(dicarboximide), and N,N'-bis(2,6-xylidyl)-3,4,9,10-perylenebis(dicarboximide).

* * * * *